US008500676B2

(12) United States Patent
Jansson et al.

(10) Patent No.: US 8,500,676 B2
(45) Date of Patent: Aug. 6, 2013

(54) DEVICE FOR CARRYING OUT A PERITONEAL DIALYSIS TREATMENT

(75) Inventors: Olof Jansson, Vellinge (SE); Pascal Bernard, Ecully (FR); Pierre-Yves Durand, Nancy (FR); Sture Hobro, Lund (SE); Eva Persson, Lund (SE); Bengt-Olov Thell, Flyinge (SE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1576 days.

(21) Appl. No.: 10/575,461

(22) PCT Filed: Oct. 13, 2004

(86) PCT No.: PCT/SE2004/001467
§ 371 (c)(1),
(2), (4) Date: Aug. 24, 2009

(87) PCT Pub. No.: WO2005/035023
PCT Pub. Date: Apr. 21, 2005

(65) Prior Publication Data
US 2010/0137782 A1    Jun. 3, 2010

(30) Foreign Application Priority Data
Oct. 13, 2003    (SE) ...................................... 0302698

(51) Int. Cl.
*A61M 1/00*    (2006.01)
(52) U.S. Cl.
USPC ................. 604/29; 210/645; 604/28; 604/30; 604/31
(58) Field of Classification Search
None
See application file for complete search history.

(56) References Cited

U.S. PATENT DOCUMENTS

| 3,730,183 | A |   | 5/1973 | Goldsmith et al. |
| 5,141,493 | A |   | 8/1992 | Jacobsen et al. |
| 5,431,626 | A | * | 7/1995 | Bryant et al. ................... 604/65 |
| 5,722,947 | A |   | 3/1998 | Jeppsson et al. |
| 6,293,921 | B1 |   | 9/2001 | Shinmoto et al. |
| 6,558,343 | B1 |   | 5/2003 | Neftel |

FOREIGN PATENT DOCUMENTS

| EP | 0 498 382 A1 | 8/1992 |
| JP | 2003-509131 | 3/2003 |
| WO | WO 95/27520 | 10/1995 |
| WO | WO 99/02206 | 1/1999 |
| WO | WO 01/19430 A1 | 3/2001 |

OTHER PUBLICATIONS

James C. Brandes, M.D., et al., "Optimization of Dialysate Flow and Mass Transfer During Automated Peritoneal Dialysis," *American Journal of Kidney Diseases*, vol. 25, No. 4 (April), 1995: pp. 603-610.
Kazuo Kumano, et al., "Minimizing the Drainage Period for Continuous Ambulatory Peritoneal Dialysis,"*Peritoneal Dialysis International*, vol. 14, 1994: pp. 52-55.
Pierre-Yves Durand, "APD Schedules and Clinical Results," *Ronco C, Dell'Aquila R, Rodighiero MP(eds): Peritoneal Dialysis Today*. Contrib Nephrol. Basel, Karager, 2003, vol. 140, pp. 272-277.

* cited by examiner

*Primary Examiner* — Dirk Bass
(74) *Attorney, Agent, or Firm* — Jacobson Holman PLLC

(57) ABSTRACT

A device and a method for a peritoneal dialysis treatment having several cycles include a cycler controlled by a processor. The cycler fills the abdominal cavity with dialysis fluid, and drains the abdominal cavity. A sensor senses a variable related to the draining of the dialysis fluid. The draining is interrupted when the variable reaches a breakpoint at which the variable is radically changed, thereby leaving the residual volume of fluid.

16 Claims, 3 Drawing Sheets

DEVICE FOR CARRYING OUT A PERITONEAL DIALYSIS TREATMENT

CROSS-REFERENCE TO RELATED APPLICATION

This is a national stage of PCT/SE2004/001467 filed Oct. 13, 2004 and published in English, which has a priority of Swedish Application No. 0302698-6 filed Oct. 13, 2003, and which claims benefit of U.S. Provisional Application No. 60/523,334 filed Nov. 20, 2003, hereby incorporated by reference.

TECHNICAL FIELD

The present invention generally refers to a tidal peritoneal dialysis treatment. More specifically, the present invention is concerned with automated tidal peritoneal dialysis.

In particular, the present invention refers to a device for carrying out a tidal peritoneal dialysis treatment of a patient in a plurality of cycles, each cycle including a fill period, a dwell period and drain period. Furthermore, the present invention refers to a method for carrying out a tidal peritoneal dialysis treatment of a patient in a plurality of cycles, each cycle including a fill period, a dwell period and drain period.

THE BACKGROUND OF THE INVENTION

Many persons suffer from different kidney diseases, which make them dependent on dialysis treatment. Among the different methods for dialysis, peritoneal dialysis, PD, has proven to be a robust method which may be performed by the dialysis patient at his home. During PD, dialysis fluid is passed to the abdominal cavity of the patient where it is allowed to reside for a predetermined time period to allow a removal of toxic substances and excess water from the patient/body. After the expiry of the predetermined time period, the dialysis fluid is removed from the peritoneal cavity and is replaced by fresh dialysis fluid. This is repeated for a number of cycles. There are a number of different techniques with different schemes for filling and emptying the peritoneal cavity. Common for the different techniques is that a volume on the order of liters for the average patient is replaced during each cycle and that there is a plurality of cycles.

PD performed with the aid of a cycler is called APD (Automated Peritoneal Dialysis), wherein the cycler performs the successive filling of dialysis fluid and draining of dialysis fluid.

One APD-method is CCPD (Continuous Cycling Peritoneal Dialysis), wherein 4-8 exchanges of dialysis fluid are performed during night and wherein the abdominal cavity is filled with dialysis fluid during the day. Each draining is a complete draining, i.e. the abdominal cavity is substantially empty before each new filling of dialysis fluid.

Another APD-method is NIPD (Nightly Intermittent Peritoneal Dialysis), wherein 5-10 exchanges of dialysis fluid are performed during night and wherein the abdominal cavity is empty during the day. Each draining is a complete draining, i.e. the abdominal cavity is substantially empty before each new filling of dialysis fluid.

A further APD-method is TPD (Tidal Peritoneal Dialysis), wherein 5-12 exchanges of dialysis fluid are performed during night and wherein the abdominal cavity is empty or filled with dialysis fluid during the day. An initial fill volume is instilled but only a part of this fill volume, e.g. 50-80%, is drained and replaced with each cycle.

Each APD-cycle looks in principle as disclosed in the attached FIG. 1. Each cycle thus consists of a fill period F, a dwell period Dw, and a drain period Dr. The fill period F, during which the dialysis fluid is supplied to the abdominal cavity with a fill volume VF, is characterised by a relatively high flow rate of the dialysis fluid. The dwell period Dw, during which the abdominal cavity is filled with dialysis fluid, is characterised by a slow increase in the fluid volume in the abdominal cavity. This increase is a result of the ultrafiltration, i.e. the osmotic net transport of fluid from the blood of the patient to the abdominal cavity. The drain period Dr, during which the spent dialysis fluid is drained out from the abdominal cavity, exhibits two phases, a first high flow phase characterised by a relatively high flow rate of dialysis fluid, and a second low flow phase characterised by a relatively slow flow rate of dialysis fluid. The two phases are clearly distinguished from each other at a breakpoint B.

During the first high flow phase, which could last for about 5-7 min, the flow rate is typically between 250 and 300 ml/min depending on the pressure, the type of machine, etc. During the second low flow phase, which could last for about 10-15 min, the flow rate is typically less than 50 ml/min.

This means that a relatively large portion of the dialysis fluid in the abdominal cavity has been drained out during a relatively short part of the total time of the drain period Dr. Furthermore, no significant dialysis takes place when there is only a relatively small volume of spent dialysis fluid in the abdominal cavity, i.e. during the second low flow phase. Consequently, the second low flow phase constitutes a waste of time of the total time of the PD-treatment.

A further problem with the second low flow phase is that the patient can suffer from abdominal pain during this phase. When the flow rate is low or zero no dynamic pressure drop will be present over the catheter and the drain line. Because of this, a suction pressure will be transmitted to the abdominal cavity, which means the catheter can be sucked against the walls of the abdominal cavity causing said pain.

PRIOR ART

U.S. Pat. No. 6,558,343 discloses a device and method aiming at an optimisation of exchange of dialysis fluid. The device is provided with a system enabling dialysis fluid exchange parameters to be varied over time so as to maintain an optimum quality of dialysis fluid, while optimising the exchange volumes so as to minimise the total consumption of dialysis liquid. This is achieved by varying the frequency of the exchange cycles, e.g. the exchange cycles, the volume changed, the total volume of dialysis fluid, the pause period between cycles, the flow rate during an exchange can be low at the start of the treatment and increase over time during treatment. The variation of the treatment is established on the basis of optimisation taking account on parameters specific to the patient under consideration (filtration curve). The parameters are determined before the actual treatment is started and are not changed during the treatment as such. In order to be able to make this determination data specific to the patient under consideration are needed. An optimal fill volume is a condition for allowing a comfortable diaphragm position and breathing for the patient.

Brandes et al in American Journal of Kidney Diseases, Vol. 25, No. 4 1995 on page 603-610 discloses findings in connection with "Optimization of Dialysate Flow and Mass Transfer During Automated Peritoneal Dialysis". More specifically, Brandes et al discloses that analysis of drain flow rate versus time revealed an initial segment of high outflow (350+/−89 mL/min) followed by an abrupt transition (hereafter referred to as breakpoint) to a segment characterised by slow drainage (36+/−21 mL/min). The first segment of drain only took 5.6+/−2.3 minutes (42% of the total drain time); in that time 83%+/−10% of the dialysis fluid was drained. It was concluded that, automated peritoneal dialysis treatment, including intermittent peritoneal dialysis which may be done in the upright position, should be done in the supine rather than upright position to optimise a mass transfer area coefficient (KoA) and shortening drain time to include only the initial segment of high outflow to improve the efficiency and convenience of therapy.

Kumano et al in Peritoneal Dialysis International Vol. 14, pp. 52-55 discloses a study where it was found that a rapid drainage for the first 5-7 minutes followed by a very slow drainage. More than 80% of the drainage was achieved within the former period. Kumano et al conclude that 10 minutes is a sufficient drainage period for most CAPD patients with 2-L dialysis fluid volume. Kumano et al suggests that the drain pattern is determined for each individual patient in order to recommend an individualised drainage time.

Durand, Pierre-Yves, in Peritoneal Dialysis Today, Vol. 140, pp. 272-277 in the article APD Schedules and Clinical Results briefly describes a future optimised tidal peritoneal dialysis treatment based on an automatic detection of the breakpoint.

WO99/02206 discloses a cycler for performing filling of dialysis fluid to the abdominal cavity of the patient and draining of the spent dialysis fluid from the patient during a PD-treatment. The cycler includes a closed chamber which may be subjected to an overpressure for the filling, and an under pressure for the draining.

SUMMARY OF THE INVENTION

The object of the present invention is to provide a method and a device for carrying out an improved tidal peritoneal dialysis treatment.

A further object is to provide a tidal peritoneal dialysis treatment that optimises the use of dialysis fluid.

A still further object is to provide a tidal peritoneal dialysis treatment that optimises the use of the time spent on the treatment.

A still further object is to provide a tidal peritoneal dialysis treatment that may be performed without any need to consider the position of the patient to be treated.

The object is achieved by the device initially defined, which includes:
- a processor;
- a cycler connected to the processor and adapted to fill the abdominal cavity of the patient with dialysis fluid, and to drain the abdominal cavity; and
- a sensor connected to the processor and adapted to sense during the draining a variable related to the draining of the dialysis fluid from the abdominal cavity;

wherein the processor is adapted to initiate interruption of the draining, at least for most of the cycles of the treatment, when the variable reaches a breakpoint at which the variable is radically changed, thereby leaving a residual volume of dialysis fluid in the abdominal cavity.

By permitting interruption of the draining at the breakpoint, the draining period may be significantly shortened in relation to a standard APD-treatment where the abdominal cavity is completely emptied. The part of the total cycle time during which an active dialysis treatment is performed will be correspondingly increased. The filling of dialysis fluid in the next cycle may thus be started immediately when the breakpoint has been reached, which means that no time will be spent which merely involves an inefficient draining of a relatively small quantity of dialysis fluid. The whole night during which the patient is sleeping may thus be used for an efficient dialysis treatment. Moreover, the abdominal pain that can occur during the low flow phase of the draining period may be avoided, which of course increases the comfort for the patient.

According to an embodiment of the invention, the device includes means for determining a first parameter concerning a desired target volume of the dialysis fluid to be contained in an abdominal cavity of the patient after each fill period of the treatment. The first parameter may, at least for the initial cycle or cycles, be determined in advance by a physician or any other suitable person, or by means of the result from a preceding treatment. The first parameter may, during the treatment, be maintained at the determined value or adjusted as explained below.

According to a further embodiment of the invention, the device includes means for determining a second parameter concerning a total volume of a dialysis fluid to be used during the remaining part of the treatment. The second parameter may, at least for the initial cycle or cycles, be determined in advance by a physician or any other suitable person, or by means of the result from a preceding treatment. The second parameter may, during the treatment, be maintained at the determined value or adjusted as explained below.

According to a further embodiment of the invention, the device includes means for determining a third parameter concerning a total length of time of the remaining part of the treatment. The third parameter may, at least for the initial cycle or cycles, be determined in advance by a physician or any other suitable person, or by means of the result from a preceding treatment. The third parameter may, during the treatment, be maintained at the determined value or adjusted as explained below.

According to a further embodiment of the invention, the device includes means for determining a fourth parameter concerning a residual volume of dialysis fluid in the abdominal cavity after the drain period. The fourth parameter may, at least for the initial cycle or cycles, be determined in advance by a physician or any other suitable person, or by means of the result from a preceding treatment. The fourth parameter may, during the treatment, be maintained at the determined value or adjusted as explained below.

According to a further embodiment of the invention, the processor is adapted to calculate for the next one of said cycles by means of the parameters a fill volume of the dialysis fluid and a fill/dwell time including the time of the fill period and the dwell period. The cycler may then be adapted to fill the abdominal cavity of the patient with the calculated fill volume of the dialysis fluid until the target volume is reached, and to drain the abdominal cavity after the calculated fill/dwell time. The device also permits adjustment of the fill/dwell time for obtaining more or fewer cycles in order to optimise the consumption of fluid and time.

According to a further embodiment of the invention, the processor is adapted to set the dwell period to a constant time value for substantially all cycles of the treatment. Some patients, e.g. the so-called "high transporters", may have a more effective peritoneum than the typical patient to be treated. This means that the dialysis fluid is relatively quickly consumed. If the dwell period is set too long, toxic substances and water may then start to flow back through the peritoneum to the patient. For such patients, the processor may thus be adapted to limit the dwell time to a maximum value. Such a limitation could reduce the total length of time of the treatment.

According to a further embodiment of the invention, the device includes means for determining an initial, fifth parameter concerning an expected ultrafiltration volume, wherein the processor is adapted to considered the fifth parameter in the calculation of the fill volume of the dialysis fluid. An expected ultrafiltration volume may be determined in advance in a relatively secure manner by means of the ultrafiltration volume of the previous treatment or treatments of the patient, the composition of the dialysis fluid etc. When considering also the ultrafiltration volume the fill volume for the next cycle may be calculated in a more exact manner.

According to a further embodiment of the invention, the processor is adapted to calculate also a number of said cycles to be performed during the remaining part of the treatment.

According to a further embodiment of the invention, the processor is adapted to make a relatively small adjustment of the target volume determined by the first means for the cycles following after the first cycle. Such a small adjustment may, for instance, be from −20 to +10% of the initial target volume, or more specifically +/−10% of the initial target volume. The processor may also be adapted, when calculating the fill volume for at least the last cycle of the treatment, to reduce significantly the fill volume, i.e. to be significantly less than the fill volume of the preceding cycles, e.g. 20-80% of a preceding cycle. The last cycle may also be divided into two cycles with a corresponding reduction of the dwell time of these cycles.

According to a further embodiment of the invention, said variable includes the flow rate of the dialysis fluid during the drain period. The breakpoint may thus in a convenient manner be sensed as an abrupt drop in the flow rate. The flow rate may for instance be sensed by sensing the weight of the drained dialysis fluid. This weight may be continuously sensed by a scale mounted in the cycler for performing the filling and the draining.

According to another embodiment of the invention, said variable includes a pressure in the abdominal cavity of the patient during the drain period. Such a pressure value may be obtained by a continuous sensing of the intraperitoneal pressure, IPP.

According to a further embodiment of the invention, the sensor is adapted to sense a drain volume of the drained dialysis fluid after the drain period and wherein the processor is adapted to calculate the residual volume by means of the drain volume, the expected ultrafiltration volume and the fill volume, and to determine a trend of the residual volume after at least two cycles. The trend is reflecting the correctness of the initially determined fifth parameter concerning the expected ultrafiltration volume. Should the said initially determined expected ultrafiltration volume have been set incorrectly, it will be shown in the said residual volume trend. The said residual volume trend may therefore be used as a safety measure to avoid overfilling of the patient. Furthermore, the processor may be adapted to adjust the expected ultrafiltration volume if the trend exhibits an increasing or decreasing value of the residual volume and if said value exceeds a predetermined first limit value.

According to a further embodiment of the invention, the cycler is adapted to drain, during a following cycle, the abdominal cavity completely so that the residual volume is substantially zero if the trend exhibits an increasing or decreasing value of the residual volume and if said value exceeds a predetermined second limit value, and wherein the processor is adapted to calculate the a new expected ultrafiltration volume based on the drain volume after the complete draining. Consequently, the safety measure mentioned above may involve a total drain in order to return to a safe state. In the said safe state it is also possible to get an exact measure of the ultrafiltration for the, to this point, completed cycles. From the said residual volume trend it is also possible to recalculate the said initially set ultrafiltration parameter to get a better value. The said residual volume is varying some from one cycle to the next, implying that the said recalculated ultrafiltration parameter can only be an estimate.

According to a further embodiment of the invention, the sensor is adapted to detect an initial value of said variable at the beginning of the drain period and a critical value of said variable, wherein the breakpoint is reached when the variable reaches the critical value. A critical flow rate may be 30-85% of the initial flow rate, e.g. 85%, 80%, 70%, 60%, 50%, 40%, 30%, 20% or 10% of the initial flow rate.

Moreover, the object is achieved by the device initially defined, which includes the features of the independent claim 18.

The object is also achieved by the method initially defined, which includes for substantially all cycles the steps of:
 filling the abdominal cavity of the patient with a fill volume of dialysis fluid;
 draining the abdominal cavity;
 sensing during the draining a variable related to the draining of the dialysis fluid leaving the abdominal cavity;
 interrupting the draining when, at least for most of the cycles of the treatment, the variable reaches a breakpoint at which the variable is radically changed; and
 leaving a residual volume of dialysis fluid in the abdominal cavity.

Advantageous further developments of the method are defined in the dependent claims 20 to 37.

Moreover, the object is achieved by the method initially defined, which includes for substantially all cycles the steps defined in the independent claim 38.

BRIEF DESCRIPTION OF THE DRAWINGS

The present invention is now to be explained more closely by means of various embodiments thereof and with reference to the drawings attached hereto.

DETAILED DESCRIPTION OF VARIOUS EMBODIMENTS OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modification within the spirit and scope of the invention will become apparent to those skilled in the art from this detailed description.

Figure 1:
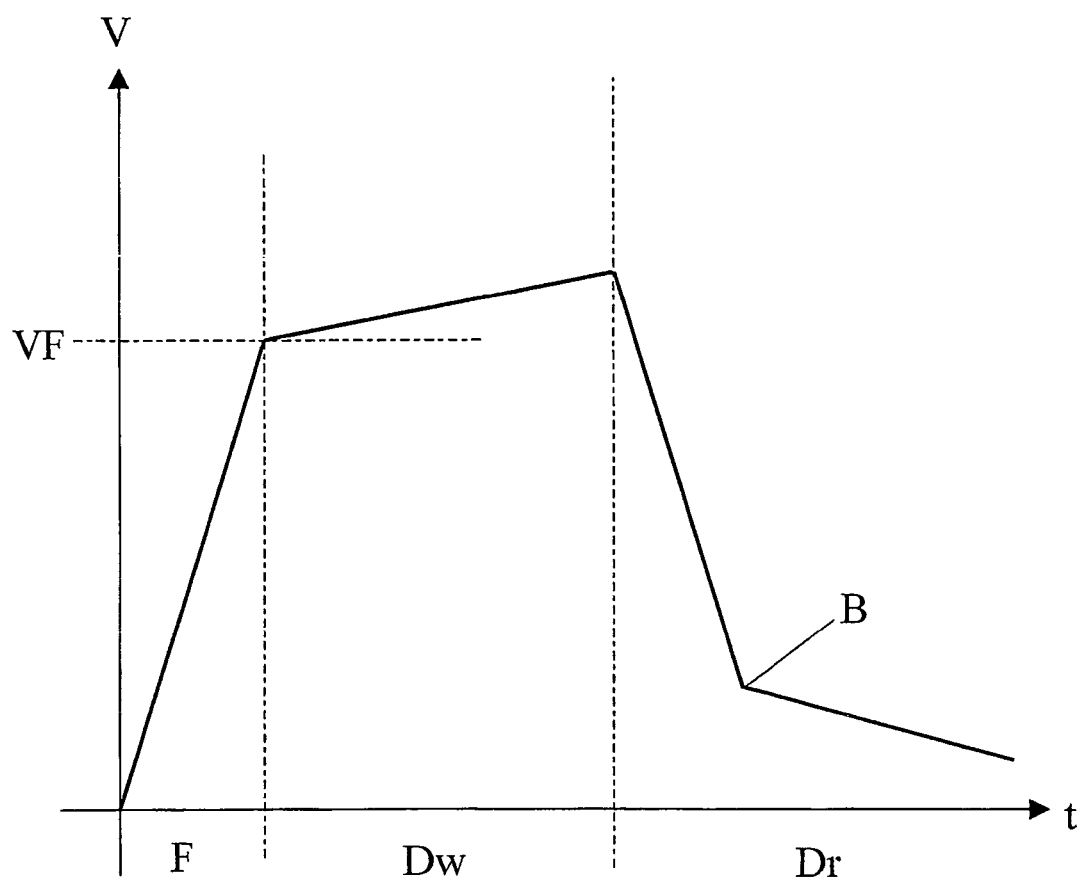
FIG. 1 shows a diagram of a PD-cycle.
Figure 2:
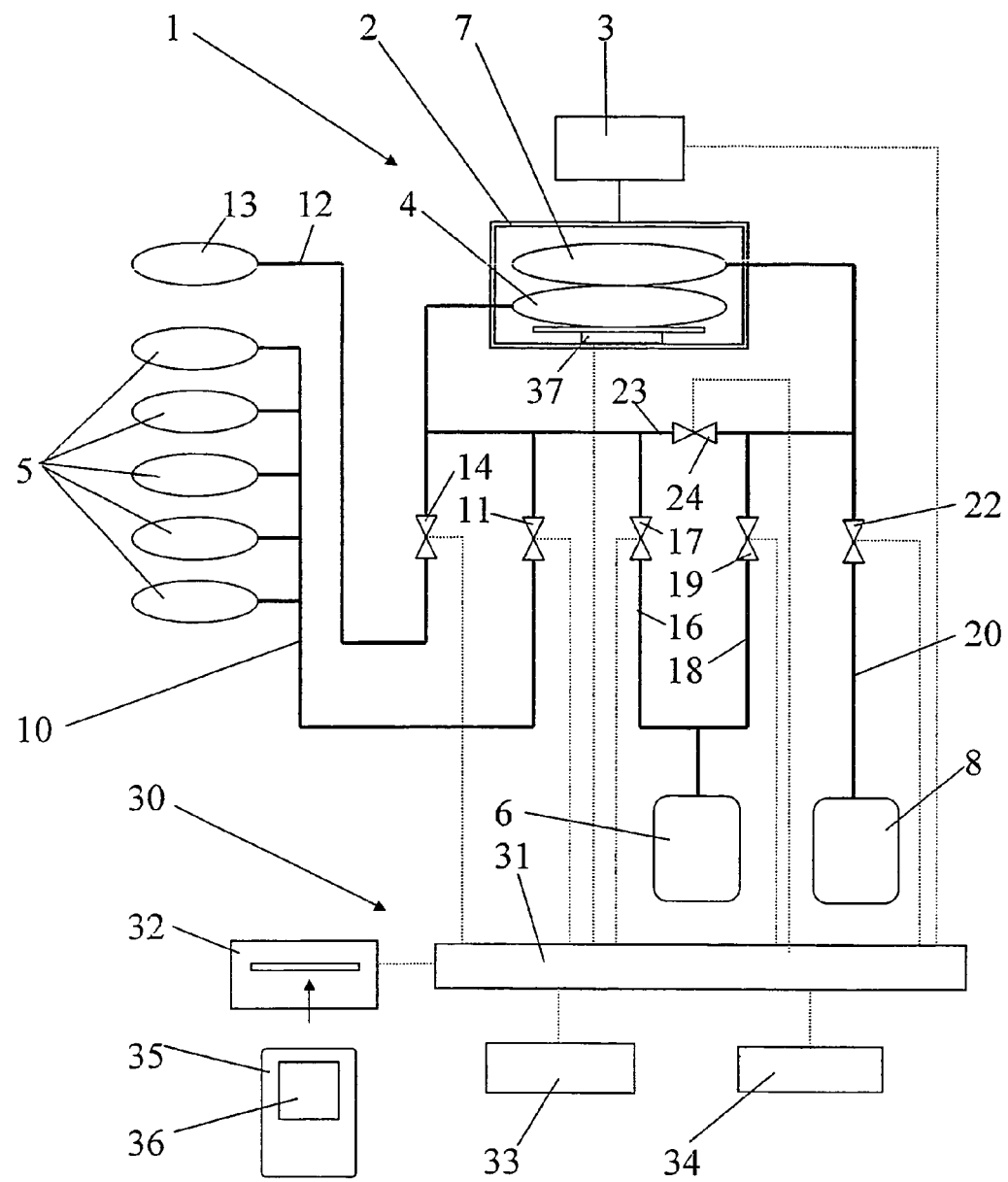
FIG. 2 shows schematically a view of a device for carrying out a tidal peritoneal dialysis treatment.

FIG. 2 discloses a peritoneal treatment system including a device for carrying out a tidal peritoneal dialysis treatment of a patient in a plurality of cycles. Such a cycle is disclosed in FIG. 1 and includes a fill period F, a dwell period Dw and drain period Dr.

The device includes a cycler 1 for performing filling of dialysis fluid to the abdominal cavity of the patient and draining of the spent dialysis fluid from the patient. The cycler 1 includes a closed chamber 2 and a pump device 3 adapted to subject the interior of the chamber 2 to an overpressure for the filling or to a sub-pressure for the draining. The chamber 2 is adapted to house a heater bag 4 arranged to receive the dialysis fluid from a number of fluid bags 5. The dialysis fluid is supplied from the heater bag 4 to a patient, illustrated by the box 6. The chamber 2 is also adapted to house a drain bag 7 arranged to receive the spent dialysis fluid form the patient 6. The spent dialysis fluid is discharge from the drain bag 7 to a drain 8.

The device includes a first conduit 10 for connecting the fluid bags 5 with the heater bag 4. The first conduit 10 is openable by means of a first heater fill valve 11. A second conduit 12 is provided for connecting an additional fluid bag 13 with the heater bag 4. The second conduit 12 is openable by means of a second heater valve 14. A third conduit 16 is provided for connecting the heater bag 4 to the patient 6. The third conduit 16 is openable by means of a patient fill valve 17. A fourth conduit 18 is provided for connecting the patient 6 to the drain bag 7. The fourth conduit 18 is openable by means of a patient drain valve valve 19. A fifth conduit 20 is provided for connecting the drain bag 7 to the drain 8. The fifth conduit 20 is openable by means of a system drain valve 22. A bypass conduit 23 is provided between the third conduit 16 and the fourth conduit 18. The bypass conduit 23 is openable by means of a bypass valve 24.

The device also includes a control unit 30 including a processor 31, an input device 32 and suitable memory 33. The processor 31 is connected to the pump device 3 and the valves 11, 14, 17, 19, 22 and 24 for controlling the treatment. The processor may also be connected to an output device 34, such as a screen, a communication device etc. to enable supervision of the treatment. Furthermore, the control unit 30 is connected to a sensor 37 for sensing the volume of the fluid in the heater bag 4 and the drain bag 7. In the embodiment disclosed the sensor 37 includes a scale provided in the pressure chamber 2 for sensing the weight, and thus the volume, of the fluid in the heater bag 4 and the drain bag 7.

The input device 32 may include a card reader arranged to receive a patient card 35 including memory means 36 for storing patient data and different parameters for the performance of the treatment. The patient card 35 may be programmed with appropriate data and parameters by the physician being responsible for the patient 6. The parameters contained in the memory means 36 may according to a first embodiment be the following:

A first parameter, concerning a desired target volume VT of the dialysis fluid to be contained in the abdominal cavity of the patient 6 after each fill period F of the treatment.

A second parameter, concerning a total volume of a dialysis fluid to be used during the treatment.

A third parameter, concerning a total length of time of the treatment.

A fourth parameter, concerning a residual volume VR of dialysis fluid in the abdominal cavity after the drain period.

A fifth parameter, concerning an expected ultrafiltration volume VU.

Alternatively, the input device 32 may, for instance, include a keyboard or a touch screen through which the actual patient data and parameters as described above may be inputted to the device.

Before start in the treatment proper, the patient drain valve 19 is open in order to ensure the discharge of any fluid in the abdominal cavity of the patient 6 to the drain bag 7, whereas the valves 11, 14, 17, 22 and 24 are closed. During a peritoneal treatment according to this invention, dialysis fluid is supplied in a first cycle from one of the fluid bags 5 to the heater bag 4 via the first conduit 10 by opening the valve 11 and generating a low pressure in the pressure chamber 2 by means of the pump device 3. The processor 31 is adapted to calculate for this cycle, by means of the parameters defined above, a fill volume VF of the dialysis fluid and a fill/dwell time including the time of the fill period and the dwell period. 3. The processor 31 is adapted to calculate also the total number of cycles to be performed during the treatment.

The calculated fill volume VF is thus supplied to the heater bag 4 and heated to a suitable temperature corresponding to the body temperature of the patient 6. The volume in the heater bag 4 is sensed by means of the scale 37, and the filling of the heater bag 4 is continued until the target volume VT has been reached. This fill volume VF of the dialysis fluid is then supplied to the patient 6 by opening the patient fill valve 17 and generating a high pressure in the chamber 2 by means of the pump device 3. The valves 14, 11, 17, 22 and 24 are closed during this filling.

During the dwell period Dr of the first cycle the heater bag 4 may be filled with new dialysis liquid from the fluid bags 5, by opening the valve 11 and keeping the valves 14, 17, 19, 22 and 24 closed. After the new filling of the heater bag 4, the system drain valve 22 may be open to ensure discharge of the fluid in the drain bag 7. After the calculated fill/dwell time the draining of the spent dialysis fluid is initiated by opening the valve 19 and keeping the valves 11, 14, 17, 22 and 24 closed.

During the draining period Dr, the scale 37 senses continuously the increasing weight of the spent dialysis fluid supplied to the drain bag 7 from the abdominal cavity of the patient 6. When the decreasing weight change reaches a breakpoint BP at which the weight is radically changed. The processor 31 initiates the interruption of the draining by sending a closing signal the patient drain valve 19. The dialysis fluid remaining in the abdominal cavity of the patient 6 is the residual volume VR. The processor 31 is preferably adapted to interrupt the draining immediately after the breakpoint has been detected.

After the interruption of the draining the filling period F of the next cycle may be initiated immediately. However, after the first cycle, the processor 31 is adapted to adjust the parameters considering the fill/dwell time and the fill volume, the drain time from start of the drain period Dr to the breakpoint BP, and the drain volume of the preceding cycle. More specifically, with regard to the first parameter the processor 31 is adapted to make a relatively small adjustment of the target volume for the remaining cycles. Such a small adjustment of the target volume may, for instance, be from −20 to +10% of the initial target volume, or more specifically +/−10% of the initial target volume. With regard to the second parameter, the total fill volume may be adjusted by +/−5%. The processor 31 may thus determine a new total fill volume for the remaining part of the treatment. With regard to the third parameter, the total length of time may be adjusted by +/−5% or by +/−10 min (which ever is the highest).

Figure 3:
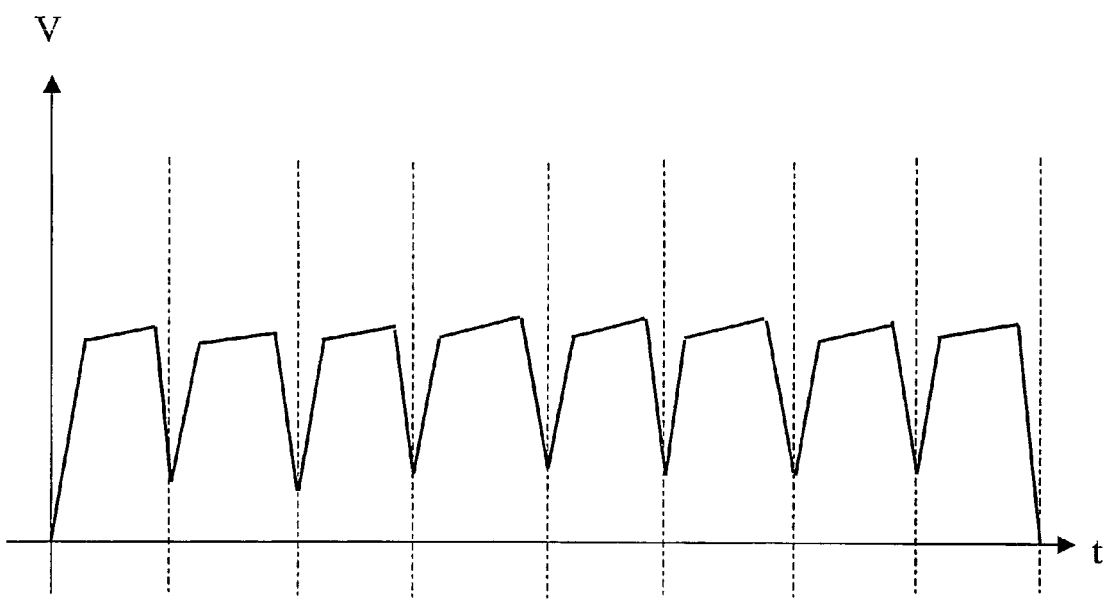
FIG. 3 shows schematically a diagram over a treatment according to the invention.

Furthermore, processor 31 is adapted to calculate, based on the adjusted parameters, the drain time and the actual drain volume, a new fill volume VF and a new fill/dwell time for the next cycle. The next cycle is then performed in a manner corresponding to the preceding cycle. After the next cycle, the steps as defined above are repeated for the remaining cycles of the treatment. An example of a full treatment is schematically disclosed in FIG. 3. As appears the target volume, the fill volume and the fill/dwell time may vary from cycle to cycle. The residual volume will vary, but the resulting residual volume will be relatively small iii comparison with the residual volume of a standard tidal peritoneal treatment.

The processor 31 may also be adapted, when calculating the fill volume for at least the last cycle of the treatment, to reduce significantly the fill volume, i.e. a reduction greater than 20% of the fill volume of the preceding cycles, e.g. about 30%, 40%, 50% or 60% of the preceding cycles. The last cycle may also be divided into two or more cycles with a corresponding reduction of the dwell time of these cycles.

The sensor 37 in the form of the scale is adapted to sense continuously the weight of the fluid delivered to the heater bag 4 and the drain bag 7. The weight change of the drained dialysis fluid is a variable that reflects the flow rate of the dialysis fluid from the patient 6 during the drain period Dr. This flow rate may also be appreciated by other means, for instance a flow meter arranged on the fourth conduit 18. A further alternative would be to sense a variable concerning a pressure in the abdominal cavity of the patient during the drain period, the so called intraperitoneal pressure IPP. However, independent on which variable is selected for the performance of the invention, the corresponding sensor is adapted to detect an initial value of the variable at the beginning of the drain period Dr. The variable is continuously sensed until a critical value has been reached. The critical value is characterised by an abrupt change of the variable, wherein this abrupt change corresponds to the breakpoint. For instance, the breakpoint may be reached at a radical drop in the flow rate or in the intraperitoneal pressure. A critical flow rate may be 30-85% of the initial flow rate, e.g. 85%, 80%, 70%, 60%, 50%, 40%, 30%, 20% or 10% of the initial flow rate.

The fifth parameter concerning the expected ultrafiltration volume is important to know in order to be able to prevent overfill of the patient 6. Overfill, i.e. a too large volume in the abdominal cavity, may cause pain or give medical drawbacks to the patient 6. An exact value of the ultrafiltration may be determined after the treatment (by letting the last drain be a complete drain), when the total fill volume and the total drain volume are known.

However, it may also be interesting to follow the residual volume over at least two cycles in order to determine the trend of said residual volume. In principle, this trend may be roughly determined by following only two cycles. Of course a better trend is achieved if the residual volume is followed over more than two cycles. The sensor 37 senses the drain volume of the drained dialysis fluid after the drain period Dr of each cycle. The processor is also adapted to calculate the residual volume by means of this drain volume, the expected ultrafiltration volume and the fill volume. Moreover, the processor is adapted to determine a trend of the residual volume after at least two cycles. The processor may also adjust the expected ultrafiltration volume if the trend exhibits an increasing or decreasing value of the residual volume and if said value exceeds a predetermined first limit value. Moreover, if the trend exhibits an increasing or decreasing value of the residual volume and if said value also exceeds a predetermined second limit value, the cycler may be adapted to drain, during a following cycle, the abdominal cavity completely so that the residual volume is substantially zero. The processor may then be adapted to calculate a new expected ultrafiltration volume based on the drain volume after the complete draining.

It is to be noted that the residual volume preferably is substantially zero before the first cycle of the treatment is started. However, the abdominal cavity may be filled with dialysis fluid before the treatment starts, wherein the first measure would be to drain out the abdominal fluid. Furthermore, the residual volume is preferably substantially zero after the last cycle of the treatment. However, the abdominal cavity may then be filled with dialysis fluid after the breakpoint treatment.

In some cases, there appears a significant variation of the residual volume of dialysis fluid in the abdominal cavity, especially at the end of the treatment. It is desirable not to have any fresh dialysis fluid left after the treatment has been terminated. If, when calculating the fill volume and the dwell time of the last cycle, the remaining volume of fresh dialysis fluid not used in the last cycle is regarded as a considerable amount, the processor 31 could be designed to divide the last cycle into two cycles as explained above. The dwell time of the last cycles may then be shortened, which means that the treatment may be terminated within the calculated total time of the treatment. If, on the other hand, the draining during the treatment regularly results in a relatively moderate draining, for instance 50% of the target volume in the abdominal cavity, and if the draining before the last cycle results in a significantly higher draining of the abdominal cavity, the processor 31 could be designed to initiate interruption of the draining of the cycle before the last cycle when a certain quantity, e.g. 50%, of the fluid in the abdominal cavity has been drained even if the breakpoint has not yet been reached in order to be able to utilise the whole length of time of the treatment.

The present invention is not limited to the embodiments disclosed, but may be varied and modified within the scope of the following claims.

What is claimed is:

1. A device for carrying out a tidal peritoneal dialysis treatment of a patient in a plurality of cycles, each cycle including a fill period (F), a dwell period (Dw) and a drain period (Dr), the device comprising:
A processor;
A cycler connected to the processor and adapted to fill the abdominal cavity of the patient with dialysis fluid, and to drain the abdominal cavity; and
A sensor connected to the processor and adapted to sense during the draining a variable related to the draining of the dialysis fluid from the abdominal cavity, said variable being a pressure in the abdominal cavity of the patient during the drain period,
The processor being adapted to initiate an interruption of the draining, at least for most of the cycles of the treatment, when the variable reaches a breakpoint at which the variable is radically changed, thereby leaving a residual volume of the dialysis fluid in the abdominal cavity.

2. The device according to claim 1, further comprising an element for determining a first parameter associated with a desired target volume of the dialysis fluid to be contained in the abdominal cavity of the patient after each filled period of the treatment.

3. The device according to claim 2, further comprising an element for determining a second parameter associated with a total volume of the dialysis fluid to be used during a remaining part of the treatment.

4. The device according to claim 3, further comprising an element for determining a third parameter associated with a total length of time of the remaining part of the treatment.

5. The device according to claim 4, further comprising an element for determining a fourth parameter associated with the residual volume of dialysis fluid in the abdominal cavity after the drain period.

6. The device according to claim 5, wherein the processor is adapted to calculate for a next one of the cycles via the parameters a fill volume (VF) of the dialysis fluid and a fill/dwell time including the time of the fill period and the dwell period.

7. The device according to claim 6, wherein the cycler is adapted to fill the abdominal cavity of the patient with the calculated fill volume of the dialysis fluid until the target volume is reached, and to drain the abdominal cavity after the calculated fill/dwell time.

8. The device according to claims 6, wherein the processor is adapted to set the dwell period to a constant time value for substantially all cycles of the treatment at least for certain patients to be treated.

9. The device according to claim 5, further comprising an element for determining an initial, fifth parameter associated with an expected ultrafiltration volume, wherein the processor is adapted to account for the fifth parameter in the calculation of the fill volume (VF) of the dialysis fluid.

10. The device according to claims 6, wherein the processor is adapted to calculate a number of the cycles to be performed during a remaining part of the treatment.

11. The device according to claims 6, wherein the processor is adapted to make a relatively small adjustment of the target volume determined by the first element for the cycles following after the first cycle.

12. The device according to claim 9, wherein the sensor is adapted to sense a drain volume of the drained dialysis fluid after the drain period, and wherein the processor is adapted to calculate the residual volume via the drain volume, the expected ultrafiltration volume and the fill volume, and to determine a trend of the residual volume after at least two of the cycles.

13. The device according to claim 12, wherein the processor is adapted to adjust the expected ultrafiltration volume if the trend exhibits an increasing or decreasing value of the residual volume and if said value exceeds a predetermined first limit value.

14. The device according to claim 12, wherein the cycler is adapted to drain, during a following cycle, the abdominal cavity completely so that the residual volume is substantially zero if the trend exhibits an increasing or decreasing value of the residual volume and if said value exceeds a predetermined second limit value, and wherein the processor is adapted to calculate a new expected ultrafiltration volume based on the drain volume after the complete draining.

15. The device according to claim 1, wherein the sensor is adapted to detect an initial value of said variable at the beginning of the drain period and a critical value of said variable, and wherein the breakpoint is reached when the variable reaches the critical value.

16. A device for carrying out a tidal peritoneal dialysis treatment of a patient in a plurality of cycles, each cycle including a fill period (F), a dwell period (Dw) and a drain period (Dr), the device comprising:

An element for determining a first parameter associated with a desired target volume of the dialysis fluid to be contained in an abdominal cavity of the patient after each fill period of the treatment;

An element for determining a second parameter associated with a total volume of a dialysis fluid to be used during a remaining part of the treatment;

An element for determining a third parameter associated with a total length of time of the remaining part of the treatment;

An element for determining a fourth parameter associated with a residual volume of the dialysis fluid in the abdominal cavity after the drain period;

A processor adapted to calculate for a next one of said cycles via the parameters a fill volume (VF) of the dialysis fluid and a fill/dwell time including the time of the fill period and the dwell period;

A cycler connected to the processor and adapted to fill the abdominal cavity of the patient with the calculated fill volume of the dialysis fluid until the target volume is reached, and to drain the abdominal cavity after the calculated fill/dwell time; and A sensor connected to the processor and adapted to sense during the draining a variable related to the draining of the dialysis fluid from the abdominal cavity, said variable being a pressure in the abdominal cavity of the patient during the drain period, The processor being adapted to initiate an interruption of the draining, at least for most of the cycles of the treatment, when the variable reaches a breakpoint at which the variable is radically changed, thereby leaving a residual volume of the dialysis fluid in the abdominal cavity.

* * * * *

UNITED STATES PATENT AND TRADEMARK OFFICE
CERTIFICATE OF CORRECTION

PATENT NO.        : 8,500,676 B2
APPLICATION NO.   : 10/575461
DATED             : August 6, 2013
INVENTOR(S)       : Jansson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2247 days.

Signed and Sealed this
Fifteenth Day of September, 2015

Michelle K. Lee
*Director of the United States Patent and Trademark Office*